(12) United States Patent
Haizmann et al.

(10) Patent No.: US 8,889,937 B2
(45) Date of Patent: Nov. 18, 2014

(54) PROCESS FOR PRODUCING ONE OR MORE ALKYLATED AROMATICS

(75) Inventors: Robert Haizmann, Rolling Meadows, IL (US); Laura E. Leonard, Western Springs, IL (US); Paula L. Bogdan, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 198 days.

(21) Appl. No.: 13/157,261

(22) Filed: Jun. 9, 2011

(65) Prior Publication Data

US 2012/0316373 A1  Dec. 13, 2012

(51) Int. Cl.
| | | |
|---|---|---|
| *C07C 2/66* | (2006.01) | |
| *C07C 5/22* | (2006.01) | |
| *C07C 5/32* | (2006.01) | |
| *C07C 5/13* | (2006.01) | |
| *C07C 7/14* | (2006.01) | |
| *C07C 5/367* | (2006.01) | |
| *C07C 7/12* | (2006.01) | |
| *C07C 6/12* | (2006.01) | |
| *C07C 5/27* | (2006.01) | |

(52) U.S. Cl.
CPC .............. *C07C 2/66* (2013.01); *C07C 2523/44* (2013.01); *C07C 2523/14* (2013.01); *C07C 2529/08* (2013.01); *C07C 2521/04* (2013.01); *C07C 5/13* (2013.01); *C07C 2521/08* (2013.01); *C07C 7/14* (2013.01); *C07C 2521/02* (2013.01); *C07C 2523/75* (2013.01); *C07C 2523/02* (2013.01); *C07C 2523/12* (2013.01); *C07C 2523/755* (2013.01); *C07C 2521/10* (2013.01); *C07C 5/367* (2013.01); *C07C 7/12* (2013.01); *C07C 6/123* (2013.01); *C07C 2529/85* (2013.01); *C07C 5/2791* (2013.01); *C07C 2523/46* (2013.01); *C07C 2523/26* (2013.01); *C07C 2101/14* (2013.01); *C07C 2529/18* (2013.01); *C07C 2523/42* (2013.01); *C07C 2521/06* (2013.01); *C07C 2523/36* (2013.01); *C07C 2523/08* (2013.01); *C07C 6/126* (2013.01); *C07C 2101/08* (2013.01)

USPC .......... 585/323; 585/319; 585/477; 585/440; 585/446

(58) Field of Classification Search
CPC ........ C07C 5/2732; C07C 15/08; C07C 2/66; C07C 2/68; C07C 2/70; C07C 15/073; C07C 5/277; C07C 5/2729; C10G 61/10; C10G 61/00; C10G 59/02; C10G 59/06
USPC ................ 585/319, 323, 300–304, 446–450, 585/477–482, 321, 489; 502/74
See application file for complete search history.

(56) References Cited

U.S. PATENT DOCUMENTS

| | | |
|---|---|---|
| 4,021,499 A | 5/1977 | Bieser |
| 4,101,595 A * | 7/1978 | Chen et al. ..................... 585/321 |

(Continued)

FOREIGN PATENT DOCUMENTS

| | | |
|---|---|---|
| EP | 1 201 730 A1 | 5/2002 |
| KR | 10-2005-0110684 A | 11/2005 |
| RU | 2 144 942 C1 | 1/2000 |

OTHER PUBLICATIONS

U.S. Appl. No. 12/689,560, filed Jan. 19, 2010, by Negiz et al., entitled, "Process for Increasing a Mole Ratio of Methyl to Phenyl".

(Continued)

*Primary Examiner* — Thuan D Dang
(74) *Attorney, Agent, or Firm* — Mark R Willis

(57) ABSTRACT

One exemplary embodiment may be a process for producing one or more alkylated aromatics. Generally, the process includes providing a first stream including an effective amount of benzene for alkylating benzene from a fractionation zone, providing a second stream including an effective amount of ethene for alkylating benzene from a fluid catalytic cracking zone, providing at least a portion of the first and second streams to an alkylation zone; and passing at least a portion of an effluent including ethylbenzene from the alkylation zone downstream of a para-xylene separation zone.

8 Claims, 1 Drawing Sheet

(56) References Cited

U.S. PATENT DOCUMENTS

| | | | |
|---|---|---|---|
| 4,107,224 A | 8/1978 | Dwyer | |
| 4,185,040 A | 1/1980 | Ward et al. | |
| 4,209,383 A | 6/1980 | Herout et al. | |
| 4,899,008 A | 2/1990 | LaPierre et al. | |
| 5,082,990 A | 1/1992 | Hsieh et al. | |
| 5,120,890 A * | 6/1992 | Sachtler et al. | 585/449 |
| 5,430,211 A | 7/1995 | Pogue et al. | |
| 5,578,195 A | 11/1996 | Tissler | |
| 5,684,580 A | 11/1997 | Cooper et al. | |
| 5,756,872 A | 5/1998 | Smith, Jr. et al. | |
| 5,847,256 A | 12/1998 | Ichioka et al. | |
| 5,869,021 A | 2/1999 | Wang et al. | |
| 5,880,320 A * | 3/1999 | Netzer | 585/448 |
| 5,977,420 A * | 11/1999 | Abichandani et al. | 585/319 |
| 5,977,423 A | 11/1999 | Netzer | |
| 6,093,866 A | 7/2000 | Wang et al. | |
| 6,143,941 A | 11/2000 | Sharma et al. | |
| 6,252,126 B1 * | 6/2001 | Netzer | 585/446 |
| 6,503,866 B1 | 1/2003 | Shepherd et al. | |
| 6,660,896 B1 * | 12/2003 | Buchanan et al. | 585/481 |
| 7,074,978 B2 | 7/2006 | Pohl | |
| 7,169,368 B1 | 1/2007 | Sullivan et al. | |
| 7,238,843 B2 | 7/2007 | Pohl | |
| 7,301,062 B2 | 11/2007 | Gartside et al. | |
| 7,393,988 B2 | 7/2008 | Hildreth et al. | |
| 7,524,467 B2 | 4/2009 | Pohl | |
| 7,525,008 B2 | 4/2009 | Bogdan et al. | |
| 7,608,745 B2 | 10/2009 | Hildreth et al. | |
| 7,632,974 B2 | 12/2009 | Schwint | |
| 7,687,674 B2 * | 3/2010 | Wegerer | 585/477 |
| 7,727,490 B2 | 6/2010 | Zhou | |
| 2003/0028059 A1 | 2/2003 | Hamper et al. | |
| 2003/0092952 A1 | 5/2003 | Netzer | |
| 2010/0012552 A1 | 1/2010 | James, Jr. et al. | |
| 2010/0018899 A1 | 1/2010 | Krupa et al. | |
| 2010/0018900 A1 | 1/2010 | Krupa et al. | |
| 2010/0018901 A1 | 1/2010 | Krupa et al. | |
| 2010/0048968 A1 | 2/2010 | Lauritzen et al. | |
| 2010/0155299 A1 | 6/2010 | Mehlberg | |
| 2010/0158767 A1 | 6/2010 | Mehlberg et al. | |

OTHER PUBLICATIONS

U.S. Appl. No. 12/689,630, filed Jan. 19, 2010, by Negiz et al., entitled, "Process for Increasing Methyl to Phenyl Mole Ratios and Reducing Benzene Content in a Motor Fuel Product".

U.S. Appl. No. 12/689,751, filed Jan. 19, 2010, by Negiz et al., entitled, "An Aromatic Aklylating Agent and an Aromatic Production Apparatus".

U.S. Appl. No. 13/105,680, filed May 11, 2011, by Leonard et al., entitled, "Process for Alkylating Benzene".

Gao, "Recent Advance in Zeolite-Based Catalytic Process in People's Republic of China", Studies in Surface Science and Catalysis, 1999, vol. 121, pp. 143-150.

Huan et al., "Vapor Phase Alkylation of Benzene with Ethylene in FCC Dry Gas over Modified ZSM-5 Zeolite Catalyst", Chemical Reaction Engineering and Technology, Oct. 2008, vol. 24, No. 5, pp. 395-399.

Stoodt et al., "UOP Sulfolane Process", Handbook of Petroleum Refining Processes, 2004, vol. 3rd Ed., pp. 2.13-2.23.

Wang et al., "Coking Kinetics on Catalyst During Alkylation of FCC Dry Gas with Benzene to Ethyl Benzene", Shiyou Huagong, 1997, vol. 26, No. 11, pp. 725-730.

Yuan, "China Prepares for the 21st Century", Hydrocarbon Processing, Mar. 1998, vol. 77, No. 3, pp. 51-53.

International Search Report and Written Opinion dated Nov. 28, 2012 for PCT/US2012/037440.

* cited by examiner

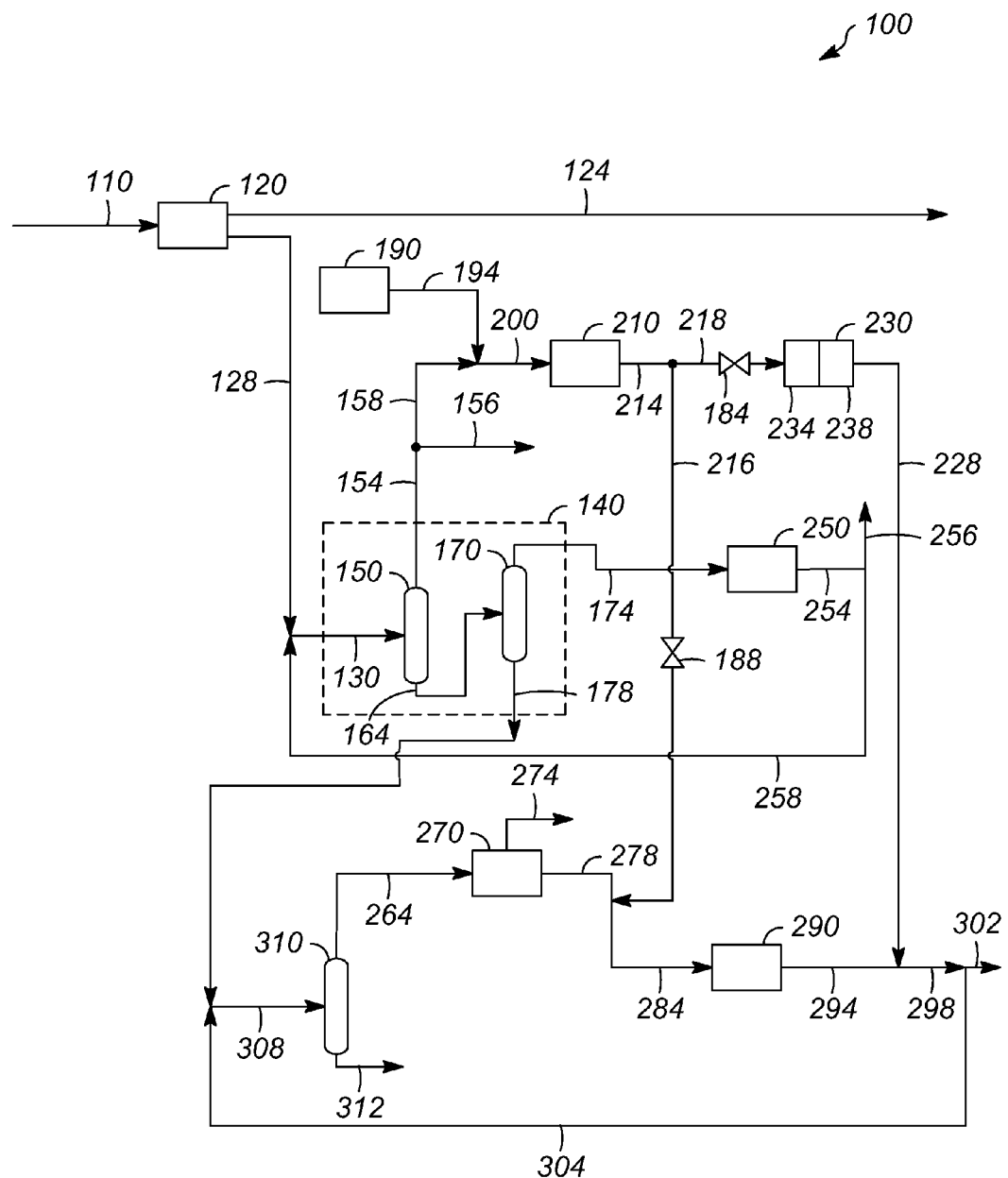

PROCESS FOR PRODUCING ONE OR MORE ALKYLATED AROMATICS

FIELD OF THE INVENTION

This invention generally relates to a process for producing one or more alkylated aromatics.

DESCRIPTION OF THE RELATED ART

A para-xylene aromatic complex can be designed to maximize yields of para-xylene for the subsequent production of polyethylene terephthalate and purified terephthalic acid fibers. Benzene, a byproduct within the aromatic complex, typically has a lower product value, which can vary greatly with market demand. Typically, the benzene:para-xylene product weight ratio may typically be about 0.2:1-about 0.5:1, by weight, depending mostly on the carbon number composition of the feed to the reforming unit. Most aromatic complexes can be integrated with oil refineries and therefore have a fairly constant feed carbon number composition. Because of this integration, the aromatic complex operator may have very little control of the benzene:para-xylene product ratio. As a consequence, there is a desire to permit greater operability control within the aromatic complex to decrease the weight ratio of benzene to para-xylene.

SUMMARY OF THE INVENTION

One exemplary embodiment may be a process for producing one or more alkylated aromatics. Generally, the process includes providing a first stream including an effective amount of benzene for alkylating benzene from a fractionation zone, providing a second stream including an effective amount of ethene for alkylating benzene from a fluid catalytic cracking zone, providing at least a portion of the first and second streams to an alkylation zone, and passing at least a portion of an effluent including ethylbenzene from the alkylation zone downstream of a para-xylene separation zone.

Another exemplary embodiment can be a process for producing one or more alkylated aromatics. Generally, the process includes providing a first stream including an effective amount of benzene for alkylating benzene from a fractionation zone, providing a second stream including an effective amount of ethene for alkylating benzene from a fluid catalytic cracking zone, providing at least a portion of the first and second streams to an ethylbenzene reaction zone to produce an effluent, and passing at least a portion of the effluent including an effective amount of ethylbenzene to an ethylbenzene conversion zone for producing one or more xylenes.

Yet another exemplary embodiment may be a process for producing one or more alkylated aromatics. The process may include providing a first stream including an effective amount of benzene for alkylating benzene from a fractionation zone, providing a second stream including an effective amount of ethene for alkylating benzene from a fluid catalytic cracking zone, providing at least a portion of the first and second streams to an alkylation zone to produce an effluent, passing at least a portion of the effluent including an effective amount of ethylbenzene to an ethylbenzene conversion zone including a first conversion stage and a second dehydrogenation stage, and passing an effluent from the ethylbenzene conversion zone downstream of a para-xylene separation zone.

The embodiments disclosed herein can reduce benzene yield and increase para-xylene production by alkylating benzene to ethylbenzene using ethene from an FCC dry gas. The ethylbenzene can be sent to a two stage ethylbenzene conversion zone to convert the ethylbenzene to one or more xylenes. Typically, the embodiments disclosed herein can include the integration of an FCC dry gas with an aromatic complex to produce ethylbenzene via benzene alkylation, optionally further integrating a two stage ethylbenzene conversion method to process the ethylbenzene to an effluent having one or more xylenes. In addition, the xylene effluent may be provided to a para-xylene separation zone and a second isomerization zone. The second isomerization zone typically contains a catalyst that isomerizes xylene and isomerizes or dealkylates ethylbenzene, and thus reduces the A8 recycle flow rate through the para-xylene separation zone and second isomerization zone loop.

DEFINITIONS

As used herein, the term "zone" can refer to an area including one or more equipment items and/or one or more sub-zones. Equipment items can include one or more reactors or reactor vessels, heaters, separators, exchangers, pipes, pumps, compressors, and controllers. Additionally, an equipment item, such as a reactor or vessel, can further include one or more zones or sub-zones.

As used herein, the term "stream" can include various hydrocarbon molecules, such as straight-chain, branched, or cyclic alkanes, alkenes, alkadienes, and alkynes, and optionally other substances, such as gases, e.g., hydrogen, or impurities, such as heavy metals. The stream can also include aromatic and non-aromatic hydrocarbons. Moreover, the hydrocarbon molecules may be abbreviated C1, C2, C3 ... Cn where "n" represents the number of carbon atoms in the hydrocarbon molecule and be further characterized by a superscript "+" or "−" symbol. In such an instance, a stream characterized, e.g., as containing C3−, can include hydrocarbons of three carbon atoms or less, such as one or more compounds having three carbon atoms, two carbon atoms, and/or one carbon atom. Also, the symbol "A" in conjunction with a numeral and/or a superscript plus or minus may be used to represent one or more aromatic compounds. As an example, the abbreviation "A9" may represent one or more aromatic C9 hydrocarbons.

As used herein, the term "aromatic" can mean a group containing one or more rings of unsaturated cyclic carbon radicals where one or more of the carbon radicals can be replaced by one or more non-carbon radicals. Exemplary aromatic compounds include benzene having a C6 ring containing three double bonds, para-xylene, ortho-xylene, meta-xylene, and ethylbenzene. Moreover, characterizing a stream or zone as "aromatic" can imply one or more different aromatic compounds.

As used herein, the term "rich" can mean an amount generally of at least about 50%, and preferably about 70%, by weight, of a compound or class of compounds in a stream.

As used herein, the term "substantially" can mean an amount generally of at least about 90%, preferably about 95%, and optimally about 99%, by weight, of a compound or class of compounds in a stream.

As used herein, the terms "naphthene", "cycloparaffin", and "cycloalkane" may be used interchangeably.

As used herein, the term "fluid catalytic cracking" may be abbreviated "FCC".

As depicted, process flow lines in the figures can be referred to interchangeably as, e.g., lines, pipes, feeds, effluents, portions, raffinates, extracts, products, or streams.

BRIEF DESCRIPTION OF THE DRAWING

The FIGURE is a schematic depiction of an exemplary aromatic production apparatus.

DETAILED DESCRIPTION

Referring to the FIGURE, an aromatic production apparatus 100 can include an aromatic extraction zone 120, a fractionation zone 140, a fluid catalytic cracking zone 190, an alkylation zone 210, an ethylbenzene conversion zone 230, a transalkylation zone 250, a para-xylene separation zone 270, an isomerization zone 290, and a fractionation zone 310. Some of these zones are disclosed in, e.g., U.S. Pat. No. 7,727,490.

Usually, a reformate fraction 110 is provided to the aromatic production apparatus 100. The reformate fraction 110 can be obtained from an overhead stream of a reformate splitter distillation column, which in turn may be obtained from a reforming zone that converts paraffins and naphthenes into one or more aromatic compounds. Typically, a reforming zone can operate at very high severity and produce about 100-about 106 research octane number gasoline reformate in order to maximize the production of one or more aromatic compounds. Generally, a hydrocarbon stream, typically a naphtha, is contacted with a reforming catalyst under reforming conditions. An exemplary reforming zone is disclosed in, e.g., U.S. Pat. No. 7,727,490.

Generally, the reformate fraction 110 can be provided to the aromatic extraction zone 120, which can provide a raffinate stream 124 and an extract stream 128. The aromatic extraction zone 120 can utilize an extraction process, such as extractive distillation, liquid-liquid extraction or a combined liquid-liquid extraction/extractive distillation process. An exemplary extraction process is disclosed in Thomas J. Stoodt et al., "UOP Sulfolane Process", Handbook of Petroleum Refining Processes, McGraw-Hill (Robert A. Meyers, 3rd Ed., 2004), pp. 2.13-2.23. Preferably, extractive distillation is utilized, which can include at least one column known as a main distillation column and may include a second column known as a recovery column.

Extractive distillation can separate components having nearly equal volatility and the same boiling point. Typically, a solvent is introduced into a main extractive distillation column above the entry point of the hydrocarbon stream being extracted. The solvent may affect the volatility of the components of the hydrocarbon stream boiling at different temperatures to facilitate their separation. Exemplary solvents include tetrahydrothiophene 1,1-dioxide, i.e., sulfolane, n-formylmorpholine, i.e., NFM, n-methylpyrrolidinone, i.e., NMP, diethylene glycol, triethylene glycol, tetraethylene glycol, methoxy triethylene glycol, or a mixture thereof. Other glycol ethers may also be suitable solvents alone or in combination with those listed above.

The aromatic extraction zone 120 can produce the extract stream 128 including one or more aromatic compounds, typically benzene and toluene, and the raffinate stream 124. Generally, the raffinate stream 124 can be sent outside the aromatic production apparatus 100 and utilized in any suitable process in a refinery or chemical manufacturing facility. The extract stream 128 can be combined with a recycle stream 258, as hereinafter described, to provide a combined stream 130 to the fractionation zone 140.

The fractionation zone 140 can include a benzene fractionation zone 150 and a toluene fractionation zone 170. Typically, the benzene fractionation and toluene fractionation zones 150 and 170 include distillation columns. The benzene fractionation zone 150 can provide an overhead stream 154 having an effective amount of benzene for alkylating and a bottom stream 164. Usually, the bottom stream 164 is provided to the toluene fractionation zone 170, as hereinafter described. The overhead stream 154 can include at least generally about 70%, preferably about 90%, and optimally about 99%, by weight, benzene. A portion may be withdrawn as a product stream 156 and another portion providing a first or benzene stream 158 to the alkylation zone 210.

The FCC zone 190 can provide an FCC dry gas stream 194 having an effective amount of ethene for alkylating, usually at least about 10%, preferably at least about 20%, by volume, ethene. One exemplary composition for the FCC dry gas stream 194 is depicted in the TABLE below:

TABLE

| Component | Weight Percent |
|---|---|
| $C_2H_4$ | 23.0 |
| $C_2H_6$ | 14.0 |
| $CH_4$ | 35.0 |
| $H_2$ | 13.0 |
| $N_2$ | 11.0 |
| CO and $CO_2$ | 2.5 |
| C3 hydrocarbons | 0.5 |
| C4 hydrocarbons | 0.5 |
| $C5^+$ hydrocarbons | 0.5 |
| $H_2S$ | <0.1 |
| $NH_3$ | <0.1 |

An exemplary FCC zone 190 is disclosed in, e.g., US 2010/0158767 or US 2010/0155299. The FCC dry gas stream 194 and the first stream 158 can form a combined alkylation feed 200. Typically, the mole ratio of benzene to ethene can be at least about 1:1, preferably about 1:1-about 20:1.

The combined alkylation feed 200 can be provided to the alkylation zone 210 using any suitable apparatus for producing ethylbenzene. Generally, the alkylation zone 210 may utilize catalytic distilling. Exemplary processes for producing ethylbenzene from benzene and ethene are disclosed in, e.g., U.S. Pat. No. 7,074,978, U.S. Pat. No. 7,238,843, and U.S. Pat. No. 7,524,467.

In one exemplary process, benzene and ethene can be provided to an adsorber, and the adsorber can, in turn, provide a bottom stream to a benzene distillation column. The benzene distillation column can provide an overhead stream that is recycled back to the adsorber. In addition, a polyethylbenzene distillation column can provide a feed to a transalkylator. The overhead of the transalkylator can again be provided to the benzene distillation column. Such a unit is disclosed in, e.g., U.S. Pat. No. 7,238,843. In some exemplary embodiments, the adsorber can be replaced with a catalytic distillation column.

The alkylation zone 210 can provide an effluent 214 that can include at least about 90%, preferably at least about 99%, by weight, ethylbenzene. Afterwards, this effluent 214 can be provided either to the isomerization zone 290 by opening a valve 188 and closing a valve 184 or the ethylbenzene conversion zone 230 by opening a valve 184 and closing a valve 188.

In one exemplary embodiment, at least a portion of the effluent 214 can be routed downstream of the para-xylene separation zone 270. As the effluent 216 contains ethylbenzene, the effluent 216 can be provided to the isomerization zone 290. In this exemplary embodiment, the isomerization zone 290 can include a catalyst that isomerizes xylene and ethylbenzene receiving a raffinate from the para-xylene separation zone 270.

Typically, the isomerization catalyst is composed of a molecular sieve component, a metal component, and an inorganic oxide component. The molecular sieve component can allow control over the catalyst performance between ethylbenzene isomerization and ethylbenzene dealkylation depending on the overall demand for benzene. Consequently, the molecular sieve may be either a zeolitic aluminosilicate or a non-zeolitic molecular sieve. The zeolite component typically is either a pentasil zeolite, which includes the structures of MFI, MEL, MTW, MTT and FER (IUPAC Commission on Zeolite Nomenclature), a beta zeolite, or a mordenite zeolite. The metal component can be a noble metal component, and may include an optional base metal modifier component in addition to the noble metal or in place of the noble metal. The noble metal may be a metal of platinum, palladium, rhodium, ruthenium, osmium, or iridium. The base metal can be of rhenium, tin, germanium, lead, cobalt, nickel, indium, gallium, zinc, uranium, dysprosium, thallium, or a mixture thereof. The base metal may be combined with another base metal, or with a noble metal. Suitable total metal amounts in the isomerization catalyst range from about 0.01-about 10%, preferably from about 0.01-about 5%, by weight. Suitable zeolite amounts in the catalyst can range from about 1-about 99%, preferably about 10-about 90%, and more preferably about 25-about 75%, by weight. The balance of the catalyst is composed of inorganic oxide binder, typically alumina. One exemplary isomerization catalyst is disclosed in, e.g., U.S. Pat. No. 7,525,008.

Typical isomerization conditions include a temperature in the range from about 0-about 600° C. and a pressure from atmospheric to about 3,450 kPa. The liquid hourly hydrocarbon space velocity of the feedstock relative to the volume of catalyst can be from about 0.1-about 30 $hr^{-1}$. Generally, the hydrocarbon contacts the catalyst in admixture with gaseous hydrogen at a hydrogen:hydrocarbon mole ratio of about 0.5:1-about 15:1 or more, and preferably a mole ratio of about 0.5:1-about 10:1. Typically, hydrogen is added to the isomerization zone 290 for isomerizing ethylbenzene.

Alternatively, if producing one or more xylenes is desired, the valve 188 can be closed and the valve 184 may be opened to provide the effluent 214 as a feed to the ethylbenzene conversion zone 230. The ethylbenzene conversion zone 230 can include a first stage 234 and a second stage 238. Although not wanting to bounded by theory, at least some of the ethylbenzene may be converted by hydrogenating and isomerizing into one or more alkylated cycloalkanes or naphthenes, such as trimethylcyclopentane or dimethylcyclohexane, in the first stage 234. In the second stage 238, these cycloalkanes or naphthenes may be dehydrogenated into one or more xylenes. The first and second stages 234 and 238 may be in a single reactor or separate reactors.

Generally, the first stage 234 can include any suitable naphthene isomerization catalyst. As an example, the catalyst can include about 2-about 90% zeolite, such as MTW zeolite, UZM-14 zeolite, or mordenite zeolite, or other support material, such as aluminum chloride, or sulfated or tungstated zirconia. Preferably about 80%, by weight, MTW zeolite catalyst is utilized and prepared in a similar manner as Example II of U.S. Pat. No. 7,525,008. The ammonium formed zeolite can be mixed with a hydrous alumina binder, such as pseudoboemite to form a composite of 80 mass parts of zeolite to 20 mass parts of alumina. The composite can be extruded to form pellets. The extrudate may be calcined in air at about 550° C. for 2 hours.

The pellets can be impregnated with any suitable metal, such as one or more metals from groups 8-10 of the Periodic Table, such as one or more noble metals of platinum, palladium, iridium, rhenium, ruthenium, and osmium, and/or nickel. Generally, the catalyst includes one or more metals in an amount of about 0.01-about 2%, by weight, based on the total weight of the catalyst. In one exemplary embodiment, the pellets may then be impregnated with an aqueous solution of chloroplatinic acid with a 3.0 mass percent hydrochloric acid to provide a platinum level of 0.3 mass percent for the final catalyst. The impregnated pellets may then be oxidized in the presence of an air stream containing about 5%, by weight, steam and a mole ratio of water:chloride of about 54:1.

The first stage 234 can operate at any suitable temperature, such as a temperature of about 50-about 350° C., preferably 275° C., any suitable pressure, such as a pressure of about 440-about 7,000 kPa, preferably about 790 kPa, any suitable effective amount of hydrogen, such as a hydrogen:hydrocarbon mole ratio of up to about 5:1, and any suitable weight hourly space velocity, such as a weight hourly space velocity of about 0.25-about 15 $hr^{-1}$, preferably about 3 $hr^{-1}$. Although not wanting to be bound by theory, the ethylbenzene may be converted to an intermediate by hydrogenation and isomerization, such as ethylcyclohexane, which can then form an equilibrium with xylene and substituted naphthenes. Preferably, this conversion is conducted at a temperature of no more than about 370° C., preferably no more than about 350° C., and optimally no more than about 300° C. to favor the equilibrium of dimethyl substituted naphthenes. Make-up hydrogen may be provided if insufficient amounts of hydrogen are present in the combined alkylation feed 200.

The second stage 238 can include any suitable reforming or xylene isomerization catalyst, which may contain about 0.01-about 2%, by weight of one or more metals, such as platinum, palladium, iridium, rhenium, ruthenium, and osmium, preferably platinum. Usually, the catalyst includes a support having a crystalline alumina. If a reforming catalyst is utilized, such a catalyst may include modifiers, such as indium, tin, lithium, iron, germanium, and/or lead, to stabilize performance at higher temperatures. One exemplary catalyst is disclosed in, e.g., U.S. Pat. No. 6,503,866. Alternatively, any bifunctional reforming catalyst, such as platinum-chlorided alumina or an aromatic isomerization catalyst, such as disclosed in, e.g., U.S. Pat. No. 7,525,008, may also be used. The xylene isomerization catalyst can include about 2-about 70%, by weight, of a zeolite or non-zeolite molecular sieve, such as MAPSO-31.

The one or more dimethyl substituted naphthene isomers can be dehydrogenated to form one or more xylenes. In one exemplary embodiment, the temperature can be at about 350-about 550° C., preferably about 425° C., a pressure of about 260-about 2,200 kPa, preferably about 790 kPa, an effective amount of hydrogen for catalyst stability, typically a hydrogen:hydrocarbon mole ratio of up to about 5:1, and a weight hourly space velocity of about 0.25-about 15 $hr^{-1}$, preferably about 2.7 $hr^{-1}$.

The fractionation zone 140 can provide an overhead stream 174 and a bottom stream 178 from the toluene fractionation zone 170. The bottom stream 178 can be combined with a recycle stream 304, as hereinafter described, and the overhead stream 174 can be provided to the transalkylation zone 250.

The transalkylation zone 250 can produce additional xylenes and benzene. Although not wanting to be bound by any theory, at least two reactions, namely disproportionation and transalkylation, can occur. The disproportionation reaction may include reacting two toluene molecules to form benzene and a xylene molecule, and the transalkylation reaction can react toluene and an aromatic C9 hydrocarbon to form two xylene molecules. As an example with respect to the transalkylation reaction, a reactant of one mole of trimethylbenzene and one mole of toluene can generate two moles of xylene, such as para-xylene, as a product. The ethyl, propyl, and higher alkyl group substituted aromatic C9-C10 can convert to lighter single-ring aromatics via dealkylation. As an example, the methylethylbenzene may lose an ethyl group through dealkylation to form toluene. Propylbenzene, butylbenzene, and diethylbenzene can be converted to benzene through dealkylation. The methyl-substituted aromatics, e.g., toluene can further convert via disproportionation or transalkylation to benzene and xylenes, as discussed above. If the feed to the transalkylation zone has more ethyl, propyl, and higher alkyl group substituted aromatics, more benzene can be generated in the transalkylation zone 250. Generally, the ethyl, propyl, and higher alkyl substituted aromatic compounds have a higher conversion rate than the methyl substituted aromatic compounds, such as trimethylbenzene and tetramethylbenzene.

In the transalkylation zone 250, the overhead stream 174 may be contacted with a transalkylation catalyst under transalkylation conditions. Preferably, the catalyst is a metal stabilized transalkylation catalyst. Such a catalyst can include a solid-acid component, a metal component, and an inorganic oxide component. Typically, the solid-acid component is a pentasil zeolite, which may include the structures of MFI, MEL, MTW, MTT and FER (IUPAC Commission on Zeolite Nomenclature), a beta zeolite, or a mordenite zeolite. Desirably, it is mordenite zeolite. Other suitable solid-acid components can include mazzite, NES type zeolite, EU-1, MAPO-36, MAPSO-31, SAPO-5, SAPO-11, and SAPO-41. Generally, mazzite zeolites include Zeolite Omega. Further discussion of the Zeolite Omega, and NU-87, EU-1, MAPO-36, MAPSO-31, SAPO-5, SAPO-11, and SAPO-41 zeolites is provided in, e.g., U.S. Pat. No. 7,169,368.

Typically, the metal component is a noble metal or base metal. The noble metal can be a metal of platinum, palladium, rhodium, ruthenium, osmium, or iridium. Generally, the base metal is rhenium, tin, germanium, lead, cobalt, nickel, indium, gallium, zinc, uranium, dysprosium, thallium, or a mixture. The base metal may be combined with another base metal, or with a noble metal. Preferably, the metal component includes rhenium. Suitable metal amounts in the transalkylation catalyst generally range from about 0.01-about 10%, preferably range from about 0.1-about 3%, and optimally range from about 0.1-about 1%, by weight. Suitable zeolite amounts in the catalyst range from about 1-about 99%, preferably from about 10-about 90%, and optimally from about 25-about 75%, by weight. The balance of the catalyst can be composed of a refractory binder or matrix that is optionally utilized to facilitate fabrication, provide strength, and reduce costs. The binder should be uniform in composition and relatively refractory. Suitable binders can include inorganic oxides, such as at least one of alumina, magnesia, zirconia, chromia, titania, boria, thoria, phosphate, zinc oxide and silica. Preferably, alumina is a binder. One exemplary transalkylation catalyst is disclosed in, e.g., U.S. Pat. No. 5,847,256.

Usually, the transalkylation zone 250 operates at a temperature of about 200-about 540° C., and a pressure of about 690-about 4,140 kPa. The transalkylation reaction can be effected over a wide range of space velocities with higher space velocities effecting a higher ratio of para-xylene at the expense of conversion. Generally, the liquid hourly space velocity is in the range of about 0.1-about 20 hr$^{-1}$. The feedstock is preferably transalkylated in the vapor phase and in the presence of hydrogen. If transalkylated in the liquid phase, then the presence of hydrogen is optional. If present, free hydrogen is associated with the feedstock and recycled hydrocarbons in a mole ratio of free hydrogen:alkylaromatic of about 0.1:1-about 10:1.

The transalkylation zone 250 can provide a transalkylation zone effluent 254. The transalkylation zone effluent 254 may be passed to a stripper or distillation column to remove a light gas stream 256, including one or more of hydrogen, methane, ethane, and ethene, with a recycle stream 258, including one or more C3$^+$ hydrocarbons, such as benzene and one or more xylenes, combined with the extract stream 128. This combined stream 130 may be provided to the fractionation zone 140.

Generally, upstream of the isomerization zone 290, a para-xylene feed stream 264 can be provided to the para-xylene separation zone 270. The para-xylene separation zone 270 may be based on a crystallization process or an adsorptive separation process. Preferably, the para-xylene separation zone 270 is based on the adsorptive separation process. Such an adsorptive separation can provide a product stream 274 containing substantially para-xylene, such as over about 99%, by weight, para-xylene. This product stream 274 may be used as a feedstock in a process to manufacture, e.g., at least one of polyethylene terephthalate and purified terephthalic acid.

The raffinate from the para-xylene separation zone 270 can be depleted of para-xylene, to a level usually less than about 1%, by weight. A raffinate stream 278 can be sent to the isomerization zone 290, where additional para-xylene is produced by reestablishing an equilibrium or near-equilibrium distribution of xylene isomers. Any ethylbenzene in the para-xylene separation unit raffinate may either be converted to additional xylenes or converted to benzene by dealkylation, depending upon the type of isomerization catalyst used.

If it is desired to provide ethylbenzene for isomerization, the valve 184 can be closed and the valve 188 opened to combine the at least a portion of the effluent 216 from the alkylation zone 210 with the raffinate stream 278. A combined feed 284 can be provided to the isomerization zone 290.

In another exemplary embodiment, the isomerization zone 290 can contain a catalyst that isomerizes xylenes and dealkylates ethylbenzene. The isomerization zone 290 can provide the effluent 294. The isomerization catalyst may include a molecular sieve and a refractory inorganic oxide. The molecular sieve can include a zeolitic aluminosilicate having an Si:Al$_2$ ratio greater than about 10, and a pore diameter of about 5 to about 8 Angstroms. Specific examples of suitable zeolites include MFI, MEL, EUO, FER, MFS, MTT, MTW, TON, MOR, and FAU. The relative proportion of zeolite in the catalyst may range from about 10-about 99%, by mass, with about 20-about 90%, by mass, being preferred. A refractory binder or matrix may be utilized and can include one or more inorganic oxides such as alumina, magnesia, zirconia, chromia, titania, boria and silica. Generally, the catalyst includes a halogen component and one or more metals, including platinum, palladium, rhodium, ruthenium, osmium, and/or iridium. The isomerization zone 290 may operate at isomerization conditions including a temperature of about 300-about 600° C., a pressure of about 100-about 5,000 kPa, and a mass hourly space velocity of about 0.5-about 100 hr$^{-1}$. Exemplary isomerization catalyst and conditions are disclosed in, e.g., U.S. Pat. No. 6,143,941.

As a consequence in one exemplary embodiment, the one or more xylenes in the at least a portion of the effluent 228 from the ethylbenzene conversion zone 230 can be provided downstream of the isomerization zone 290. A combined stream 298 can then be recycled after passing at least a portion of the combined stream 298 through fractionation to provide a stream 302 including one or more CT hydrocarbons and the recycle stream 304 including one or more C8' hydrocarbons. The recycle stream 304 may optionally be further fractionated before being combined with the bottom stream 178 to form a xylene feed stream 308. Alternatively, the recycle stream 304 can be provided directly to the fractionation zone 310.

The xylene feed stream 308 can be provided to the fractionation zone 310, including one or more xylene splitter columns. The fractionation zone 310 can provide a bottom stream 312 including one or more C9+ hydrocarbons and an overhead stream including one or more C8− hydrocarbons, which can be provided as at least a portion of the para-xylene feed stream 264. Fractionation provided downstream of an isomerization zone to provide at least a portion of its effluent to a para-xylene separation zone is disclosed in, e.g., U.S. Pat. No. 7,727,490.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for producing one or more alkylated aromatics, comprising:
A) providing a first stream comprising an effective amount of benzene for alkylating benzene from a first fractionation zone comprising a benzene fractionation zone and a toluene fractionation zone included in an aromatic production apparatus;
B) providing a second stream comprising an effective amount of ethene for alkylating benzene from a fluid catalytic cracking zone;
C) providing at least a portion of the first and second streams to an alkylation zone to produce an effluent containing ethylbenzene, wherein the alkylation zone comprises catalytic distillation;
D) passing at least a portion of the effluent comprising an effective amount of ethylbenzene to an ethylbenzene conversion zone for producing one or more xylenes; wherein the ethylbenzene conversion zone comprises a first stage and a second stage wherein the first stage converts ethylbenzene to form one or more naphthenes and the second stage dehydrogenates the one or more naphthenes to produce xylenes;
E) providing a bottom stream from the toluene fractionation zone to a second fractionation zone including one or more xylene splitter columns; and
F) passing a para-xylene feed stream from the second fractionation zone including one or more xylene splitter columns to a para-xylene separation zone that provides a product stream containing para-xylene and a raffinate stream depleted of para-xylene;

and further comprising providing an effluent comprising at least 90% by weight ethylbenzene from the ethylbenzene conversion zone downstream of an isomerization zone, combining the effluent with an isomerization zone effluent, and passing the combined effluent stream to the para-xylene separation zone to recover para-xylene.

2. The process according to claim 1, wherein the ethylbenzene conversion zone comprises a catalyst, in turn comprising a zeolite and a noble metal.

3. The process according to claim 1, wherein the effluent comprises at least about 90%, by weight, ethylbenzene.

4. The process according to claim 1, wherein the first stage operates at a temperature of no more than about 370° C.

5. The process according to claim 1, wherein the first stage operates at a temperature of no more than about 350° C.

6. The process according to claim 1, wherein the first stage operates at a temperature of no more than about 300° C.

7. The process according to claim 1, wherein the isomerization zone is downstream from the para-xylene separation zone, and further comprising providing a product stream comprising para-xylene from the para-xylene separation zone for manufacturing at least one of polyethylene terephthalate and purified terephthalic acid.

8. A process for producing one or more alkylated aromatics, comprising:
A) providing a first stream comprising an effective amount of benzene for alkylating benzene from a first fractionation zone comprising a benzene fractionation zone and a toluene fractionation zone comprised in an aromatic production apparatus;
B) providing a second stream comprising an effective amount of ethene for alkylating benzene from a fluid catalytic cracking zone;
C) providing at least a portion of the first and second streams to an alkylation zone to produce an effluent containing ethylbenzene, wherein the alkylation zone comprises catalytic distillation;
D) passing at least a portion of the effluent comprising an effective amount of ethylbenzene to an ethylbenzene conversion zone comprising a first conversion stage and a second dehydrogenation stage to produce xylenes, wherein the ethylbenzene conversion zone comprises a first stage and a second stage wherein the first stage converts ethylbenzene to form one or more naphthenes and the second stage dehydrogenates the one or more naphthenes to produce xylenes;
E) providing a bottom stream from the toluene fractionation zone to a second fractionation zone including one or more xylene splitter columns;
F) passing a para-xylene feed stream from the second fractionation zone including one or more xylene splitter columns to a para-xylene separation zone that provides a product stream containing para-xylene and a raffinate stream depleted of para-xylene;
G) passing an effluent from the ethylbenzene conversion zone to the second fractionation zone including one or more xylene splitter columns; and
H) recycling at least a portion of the ethylbenzene conversion zone effluent to the para-xylene separation zone.

* * * * *